United States Patent [19]
Tanaka et al.

[11] Patent Number: 5,874,649
[45] Date of Patent: Feb. 23, 1999

[54] PROCESS FOR PREPARING UNSATURATED ALCOHOL

[75] Inventors: Shigeyoshi Tanaka; Shinji Kotachi; Junji Koshino; Junko Yamamoto, all of Wakayama, Japan

[73] Assignee: Kao Corporation, Tokyo, Japan

[21] Appl. No.: 945,674

[22] PCT Filed: Mar. 5, 1997

[86] PCT No.: PCT/JP97/00669

§ 371 Date: Nov. 5, 1997

§ 102(e) Date: Nov. 5, 1997

[87] PCT Pub. No.: WO97/32836

PCT Pub. Date: Sep. 12, 1997

[30] Foreign Application Priority Data

Mar. 5, 1996 [JP] Japan .................................. 8-047272

[51] Int. Cl.⁶ .................................. C07C 35/06
[52] U.S. Cl. .................. 568/838; 568/700; 568/840; 568/799; 568/875; 568/881
[58] Field of Search .................. 568/840, 700, 568/838, 875, 881, 799

[56] References Cited

FOREIGN PATENT DOCUMENTS

| | | |
|---|---|---|
| 55-036423 | 3/1980 | Japan . |
| 55-139330 | 10/1980 | Japan . |
| 56-36176 | 8/1981 | Japan . |

*Primary Examiner*—Michael L. Shippen
*Attorney, Agent, or Firm*—Oblon, Spivak, McClelland, Maier & Neustadt, P.C.

[57] ABSTRACT

The object of the present invention resides in efficiently providing unsaturated alcohol from an α,β-unsaturated aldehyde.

The present invention provides a process for preparing unsaturated alcohol by selectively reducing the aldehyde group of an α,β-unsaturated aldehyde in the presence of a primary or a secondary alcohol having 2 to 8 carbon atoms using an aluminum alcoholate to produce an unsaturated alcohol such as compounds represented by the formula (III).

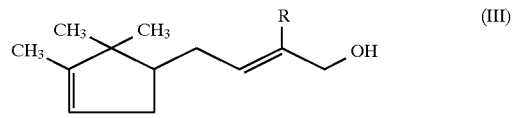

(wherein R represents an alkyl group having 1 to 3 carbon atoms)

wherein the reaction is carried out with addition of a protonic acid.

15 Claims, No Drawings

PROCESS FOR PREPARING UNSATURATED ALCOHOL

BACKGROUND OF THE INVENTION

1. Field of the Invention

The present invention relates to a process for preparing an unsaturated alcohol, preferably to a process to efficiently prepare an unsaturated alcohol by selectively reducing the aldehyde group of an α,β-unsaturated aldehyde compound.

2. Description of Related Art

For preparing the unsaturated alcohols, a process is known, wherein the aldehyde group of an α,β-unsaturated aldehyde compound is selectively reduced. Particularly, an unsaturated alcohol having 2,2,3-trimethyl-3-cyclopenten-1-yl group represented by the formula (I):

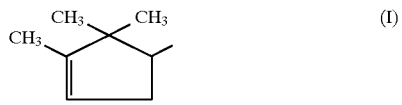

is known to be a perfume having musk-like smell as well as sandalwood-like smell, and prepared by selectively reducing the aldehyde group alone of an α,β-unsaturated aldehyde compound having 2,2,3-trimethyl-3-cyclopenten-1-yl group represented by the above formula (I).

For example, JP-B 56-36176 discloses a process for preparing 2-methyl-4-(2,2,3-trimethyl-3-cyclopenten-1-yl)-2-buten-1-ol represented by the formula (III'):

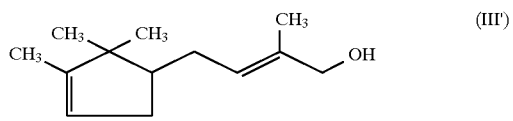

by selectively reducing the aldehyde group alone of 2-methyl-4-(2,2,3-trimethyl-3-cyclopenten-1-yl)-2-buten-1-al represented by the formula (II'):

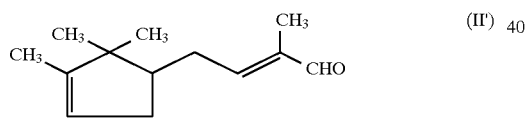

using aluminum alcoholate or a metal hydride compound in the presence of isopropyl alcohol.

This method, however, utilizes a large amount of aluminum alcoholate or a metal hydride compound as much as 40 mol % of the aldehyde as the starting material, as well as a large excess of isopropyl alcohol, i.e., more than 20 times by mole the amount of the aldehyde as the starting material, that is, this method is not efficient with low productivity.

DISCLOSURE OF THE INVENTION

An object of the present invention is to provide a process for efficient preparing an unsaturated alcohol from an α,β-unsaturated aldehyde compound.

The present inventors have studied intensively to solve the above problems and, as the results, have attained the present invention.

That is, the present invention provides a process for preparing an unsaturated alcohol from an α,β-unsaturated aldehyde compound using an aluminum alcoholate in the presence of a primary or secondary alcohol having 2 to 8 carbon atoms by selective reduction of the aldehyde group, wherein the reaction is carried out with addition of a protonic acid.

In other words, the present invention provides a process for preparing of an unsaturated alcohol by selective reduction of the aldehyde group of an α,β-unsaturated aldehyde compound in the presence of a primary or secondary alcohol having 2 to 8 carbon atoms, an aluminum alcoholate and a protonic acid.

DETAILED DESCRIPTION OF THE INVENTION

The mode for carrying out the present invention will be illustrated in detail.

Preferably, the present invention is a process for preparing an unsaturated alcohol by selectively reducing the aldehyde group of an α,β-unsaturated aldehyde compound in the presence of 0.7 to 15 times by mole of the amount of the primary or secondary alcohol having 2 to 8 carbon atoms, 0.5 to 35 mol % of the aluminum alcoholate and 0.005 to 30 mol % of the protonic acid, based on the α,β-unsaturated aldehyde compound.

The α,β-unsaturated aldehyde used in the present invention is not particularly limited so long as it may be an aldehyde having an unsaturated bond at α,β-position of the aldehyde group. Typical examples include compounds having 2,2,3-trimethyl-3-cyclopenten-1-yl group represented by the above formula (I).

The process according to the present invention may be preferably applied to the reaction to obtain 2-alkyl-4-(2,2,3-trimethyl-3-cyclopenten-1-yl)-2-buten-1-ol represented by the formula (III):

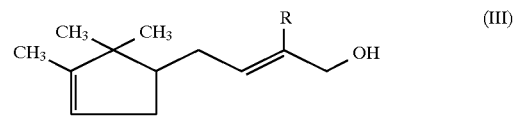

(wherein R represents an alkyl group having 1 to 3 carbon atoms)

utilizing 2-alkyl-4-(2,2,3-trimethyl-3-cyclopenten-1-yl)-2-buten-1-al represented by the formula (II):

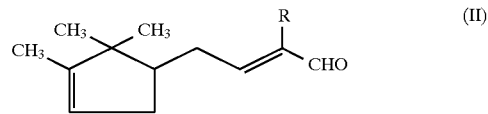

(wherein R is defined as above) as the α,β-unsaturated aldehyde.

In the above formulae (II) and (III), R represents an alkyl group having 1 to 3 carbon atoms such as methyl group, ethyl group, propyl group, isopropyl group, preferably methyl group, ethyl group. Methyl group is especially preferred.

The unsaturated alcohol represented by the formula (III) may be used as a perfume, and those prepared by the present reaction have slightly clear perfume.

The primary or secondary alcohol having 2 to 8 carbon atoms used in the present invention is aliphatic alcohol, especially including ethyl alcohol, n-propyl alcohol, isopropyl alcohol, 2-butyl alcohol, 3-methyl-2-pentyl alcohol and 3-hexyl alcohol. Secondary alcohol, particularly, isopropyl alcohol, 2-butyl alcohol, and 3-hexyl alcohol are preferred.

The aluminum alcoholate used in the present invention may be any one, preferably having alcoholate having 1 to 5 carbon atoms, for example, aluminum trimethylate, aluminum triethylate, aluminum tripropylate, aluminum triisopropylate, aluminum tributylate, aluminum triisobutylate, sec-butoxyaluminum diisopropylate.

Particularly, aluminum triisopropylate, sec-butoxyaluminum diisopropylate are preferred, and aluminum triisopropylate is most preferable from the viewpoint of yield.

In the process of the present invention, the aluminum alcoholate is used in the range preferably from 0.5 to 35 mol %, more preferably from 1 to 25 mol % based on the α,β-unsaturated aldehyde.

In the process of the present invention, the amount of the primary or secondary alcohol having 2 to 8 carbon atoms to be added is in preferably 0.7 to 15 times by mole, more preferably 1 to 10 times by mole as much an amount as the α,β-unsaturated aldehyde.

The protonic acids used in the present invention include, for example, haloacetic acid compounds such as trichloroacetic acid, dichloroacetic acid, chloroacetic acid, trifluoroacetic acid, difluoroacetic acid and fluoroacetic acid; mineral acid compounds such as hydrochloric acid and sulfuric acid; hydrocarbon sulfonic acid compounds such as trifluoromethanesulfonic acid, p-toluenesulfonic acid and methanesulfonic acid; and lower aliphatic carboxylic acid compounds such as acetic acid and propionic acid. Strong acids such as trichloroacetic acid, trifluoroacetic acid, sulfuric acid and methanesulfonic acid are preferred and, among them, trichloroacetic acid and sulfuric acid, which have high boiling point, are still preferred because they do not vaporize even at high temperature.

In the process of the present invention, the protonic acid is used, preferably in the range from 0.005 to 30 mol %, more preferably 0.01 to 10 mol %, based on the α,β-unsaturated aldehyde.

In the present invention, reaction may be preferably carried out at the temperature from 0° to 150° C., preferably 10° to 120° C., while the carbonyl compound such as acetone derived from the lower alcohol produced by the reaction is removed by distillation. Further, in the present invention, it is particularly preferred to use trichloroacetic acid or sulfuric acid, which has relatively high boiling point, and to carry out reaction while the above carbonyl compound produced by the reaction is removed by distillation. When the carbonyl compound having high boiling point is produced, it is more preferable to carry out reaction under reduced pressure.

A solvent is not always required. If required, inert solvents such as toluene and xylene may be used.

In the process of the present invention, the unsaturated alcohol can be efficiently prepared from the α,β-unsaturated aldehyde using smaller amount of the primary or secondary alcohol having 2 to 8 carbon atoms and the aluminum alcoholate, compared with that used in the conventional methods.

Separation of the objective compound from the reaction mixture can be readily carried out according to the ordinary method such as decomposition of the aluminum alcoholate with acid followed by rectification etc.

EXAMPLES

The present invention will be illustrated in detail in the following examples, but the present invention is not construed to be limited to these examples.

Example 1

2.04 g (10 mmol) of aluminum isopropylate [Al(O-i-Pr)$_3$] and 10 ml of toluene were fed into a 30 ml two-necked round bottom flask under atmosphere of nitrogen, and stirred at room temperature, and then 9.6 g (50 mmol) of 2-methyl-4-(2,2,3-trimethyl-3-cyclopenten-1-yl)-2-buten-1-al, then 0.17 g (1.5 mmol) of trifluoroacetic acid, and further 3.0 g (50 mmol) of isopropyl alcohol were added while stirring at room temperature. After 5 hours, analysis by GLC showed that 62 % of 2-methyl-4-(2,2,3-trimethyl-3-cyclopenten-1-yl)-2-buten-1-ol was obtained (corresponding to 85% selectivity for conversion of the aldehyde as the starting material).

The product had a clear and strong sandalwood-like perfume.

Example 2

The reaction was carried out in the same manner as in Example 1, except that 0.25 g (1.5 mmol) of trichloroacetic acid was used instead of trifluoroacetic acid. After 5 hours, according to GLC analysis, 61% of 2-methyl-4-(2,2,3-trimethyl-3-cyclopenten-1-yl)-2-buten-1-ol was obtained (corresponding to 87% selectivity for conversion of the aldehyde as the starting material).

The product had a clear and strong sandalwood-like perfume.

Example 3

The reaction was carried out in the same manner as in Example 1, except that toluene was not added. After 5 hours, according to GLC analysis, 67% of 2-methyl-4-(2,2,3-trimethyl-3-cyclopenten-1-yl)-2-buten-1-ol was obtained (corresponding to 91% selectivity for conversion of the aldehyde as the starting material).

The product had a clear and strong sandalwood-like perfume.

Example 4

The reaction was carried out in the same manner as in Example 1, except that 2.18 g (10 mmol) of sec-butoxyaluminum diisopropylate was used instead of aluminum isopropylate, and 10.3 g (50 mmol) of 2-ethyl-4-(2,2,3-trimethyl-3-cyclopenten-1-yl)-2-buten-1-al was used instead of 2-methyl-4-(2,2,3-trimethyl-3-cyclopenten-1-yl)-2-buten-1-al. After 5 hours, according to GLC analysis, 60% of 2-ethyl-4-(2,2,3-trimethyl-3-cyclopenten-1-yl)-2-buten-1-ol was obtained (corresponding to 87% selectivity for conversion of the aldehyde as the starting material).

The product also had a clear sandalwood-like perfume.

Comparative Example

The reaction was carried out in the same manner as in Example 1, except that trifluoroacetic acid was not added. After 5 hours, according to GLC analysis, 2% of 2-methyl-4-(2,2,3-trimethyl-3-cyclopenten-1-yl)-2-buten-1-ol was obtained.

Example 5

3.07 g (15 mmol) of Al(O-i-Pr)$_3$ and 30 ml of toluene were fed into a 100 ml four-necked round bottom flask under atmosphere of nitrogen, and stirred at room temperature, and then 28.8 g (150 mmol) of 2-methyl-4-(2,2,3-trimethyl-3-cyclopenten-1-yl)-2-buten-1-al, then 0.25 g (1.5 mmol) of trichloroacetic acid, and further 18.0 g (300 mmol) of isopropyl alcohol were added while stirring at room temperature. Reaction was conducted while fraction containing acetone generated at the solution temperature of 80° to 92° C. was distilled off. After 6 hours, the reaction solution was analyzed by GLC, 81% of 2-methyl-4-(2,2,3-trimethyl-3- cyclopenten-1-yl)-2-buten-1-ol was obtained (corresponding to 90% selectivity for conversion of the aldehyde as the starting material).

The product had a clear and strong sandalwood-like perfume.

Example 6

The reaction was carried out in the same manner as in Example 3, except that the amount of aluminum isopropoxide and trifluoroacetic acid was reduced to 1.02 g (5 mmol) and 0.06 g (0.5 mmol), respectively. After 5 hours, according to GLC analysis, 40% of 2-methyl-4-(2,2,3-trimethyl-3 -cyclopenten-1-yl)-2-buten-1-ol was obtained (corresponding to 93% selectivity for conversion of the aldehyde as the starting material).

Example 7

The reaction was carried out in the same manner as in Example 6, except that the reaction temperature was changed to 60° C. After 5 hours, according to GLC analysis, 55% of 2-methyl-4-(2,2,3-trimethyl-3-cyclopenten-1-yl)-2-buten-1-ol was obtained (corresponding to 83% selectivity for conversion of the aldehyde as the starting material).

Example 8

The reaction was carried out in the same manner as in Example 7, except that 0.05 g (0.5 mmol) of sulfuric acid was used instead of trifluoroacetic acid. After 5 hours, according to GLC analysis, 58% of 2-methyl-4-(2,2,3-trimethyl-3-cyclopenten-1-yl)-2-buten-1-ol was obtained (corresponding to 85% selectivity for conversion of the aldehyde as the starting material).

Example 9

The reaction was carried out in the same manner as in Example 7, except that 0.05 g of (0.5 mmol) methanesulfonic acid was used instead of trifluoroacetic acid. After 5 hours, according to GLC analysis, 54% of 2-methyl-4-(2,2,3-trimethyl-3-cyclopenten-1-yl)-2-buten-1-ol was obtained (corresponding to 85% selectivity for conversion of the aldehyde as the starting material).

Example 10

The reaction was carried out in the same manner as in Example 6, except that 3.7 g (50 mmol) of 2-butanol was used instead of IPA. After 5 hours, according to GLC analysis, 45% of 2-methyl-4-(2,2,3-trimethyl-3-cyclopenten-1-yl)-2-buten-1-ol was obtained (corresponding to 94% selectivity for conversion of the aldehyde as the starting material).

Example 11

The reaction was carried out in the same manner as in Example 6, except that 4.4 g (50 mmol) of 3-hexyl alcohol was used instead of IPA. After 5 hours, according to GLC analysis, 48% of 2-methyl-4-(2,2,3-trimethyl-3-cyclopenten-1-yl)-2-buten-1-ol was obtained (corresponding to 94% selectivity for conversion of the aldehyde as the starting material).

Example 12

10.2 g (50 mmol) of Al(O-i-Pr)$_3$, 0.25g (2.5 mmol) of sulfuric acid and 180 g (3.0 mol) of IPA were fed into a 1000 ml four-necked round bottom flask under atmosphere of nitrogen, and stirred at 85° C., and then 192 g (1.0 mol) of 2-methyl-4-(2,2,3-trimethyl-3-cyclopenten-1-yl)-2-buten-1-al was added. The reaction was conducted while fraction containing acetone generated at the solution temperature of 85° to 95° C. was removed by distillation. After 7 hours, the reaction solution was analyzed by GLC, 88% of 2-methyl-4 -(2,2,3-trimethyl-3-cyclopenten-1-yl)-2-buten-1-ol was obtained (corresponding to 92% selectivity for conversion of the aldehyde as the starting material).

We claim:

1. A process for preparing an unsaturated alcohol from an α,β-unsaturated aldehyde, which comprises selectively reducing the aldehyde group of said α,β-unsaturated aldehyde in the presence of a primary or secondary alcohol having 2 to 8 carbon atoms, and aluminum alkoxide, with addition of a protonic acid, wherein said aluminum alkoxide is used in an amount of from 0.5 to 35 mol % based upon the α,β-unsaturated aldehyde.

2. The process as claimed in claim 1, wherein the α,β-unsaturated aldehyde is a compound having 2,2,3-trimethyl-3-cyclopenten-1-yl group represented by the formula (I):

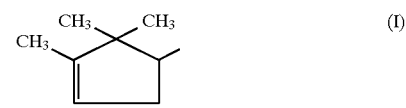

3. The process as claimed in claim 1, wherein the α,β-unsaturated aldehyde is 2-alkyl-4-(2,2,3-trimethyl-3-cyclopenten-1-yl)-2-buten-1-al represented by the formula (II):

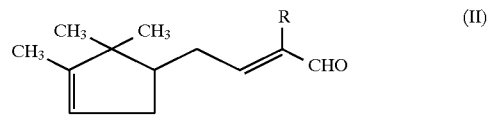

wherein R represents an alkyl group having 1 to 3 carbon atoms, and the unsaturated alcohol is 2-alkyl-4-(2,2,3-trimethyl-3-cyclopenten-1-yl)-2-buten-1-ol represented by the formula (III):

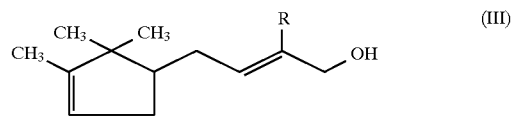

wherein R is defined as above.

4. The process as claimed in claim 3, wherein R is methyl group or ethyl group.

5. The process as claimed in claim 1, wherein the aluminum alcoholate is aluminum triisopropylate or sec-butoxyaluminum diisopropylate.

6. The process as claimed in claim 1, wherein the protonic acid is trichloroacetic acid, trifluoroacetic acid, methanesulfonic acid or sulfuric acid.

7. The process as claimed in claim 1, wherein the reaction is carried out while a carbonyl compound derived from the primary or secondary alcohol having 2 to 8 carbon atoms, produced by the reaction, is being removed by distillation.

8. The process as claimed in claim 1, wherein the primary or secondary alcohol having 2 to 8 carbon atoms is isopropyl alcohol, 2-butyl alcohol or 3-hexyl alcohol.

9. The process as claimed in claim 1, wherein the primary or secondary alcohol having 2 to 8 carbon atoms is used in 0.7 to 15 times by mole as much an amount as the α,β-unsaturated aldehyde; the aluminum alcoholate is used in an amount of 0.5 to 35 mol % per the α,β-unsaturated aldehyde; and the protonic acid is used in an amount of 0.005 to 30 mol % per the α,β-unsaturated aldehyde.

10. The process as claimed in claim 1, wherein the protonic acid is selected from the group consisting of trichloroacetic acid, dichloroacetic acid, chloroacetic acid, trifluoroacetic acid, difluoroacetic acid, fluoroacetic acid, hydrochloric acid, sulfuric acid, trifluoromethanesulfonic acid, p-toluenesulfonic acid, methanesulfonic acid, acetic acid and propionic acid.

11. The process as claimed in claim 1, wherein the protonic acid is selected from the group consisting of a haloacetic acid, a mineral acid, a hydrocarbon sulfonic acid and a lower aliphatic carboxylic acid.

12. The process as claimed in claim 9, wherein the protonic acid is used in an amount of from 0.01 to 10 mol % based on the α,β-unsaturated aldehyde.

13. The process as claimed in claim 1, which is effected at a temperature of from 0° C. to 150° C.

14. The process as claimed in claim 13, which is effected at a temperature of from 10° C. to 120° C.

15. The process as claimed in claim 1, wherein the protonic acid is trifluoroacetic acid.

* * * * *